United States Patent [19]
Tajiri et al.

[11] Patent Number: 5,423,777
[45] Date of Patent: Jun. 13, 1995

[54] PUNCTUM PLUG

[76] Inventors: Akira Tajiri, 19371 E. Parlier Ave., Reedley, Calif. 93654; Murad A. Sunalp, 6095 N. Bungalow La., Fresno, Calif. 93704

[21] Appl. No.: 143,862

[22] Filed: Oct. 27, 1993

[51] Int. Cl.$^6$ ............................................. A61M 5/00
[52] U.S. Cl. ........................ 604/294; 604/891.1; 606/107; 606/191; 606/213; 623/11
[58] Field of Search .................. 604/294, 104–107, 604/250, 264, 891.1; 606/1, 191, 107, 213; 623/11

[56] References Cited

U.S. PATENT DOCUMENTS

| | | |
|---|---|---|
| D. 295,445 | 4/1988 | Freeman . |
| 3,463,141 | 8/1969 | Mozolf . |
| 3,703,898 | 11/1972 | Zackheim . |
| 3,721,229 | 3/1973 | Panzer . |
| 3,726,284 | 4/1973 | Parker . |
| 3,858,571 | 1/1975 | Rudolph . |
| 3,949,750 | 4/1976 | Freeman . |
| 4,281,658 | 8/1981 | Child . |
| 4,660,546 | 4/1987 | Herrick et al. . |
| 4,915,684 | 4/1990 | Mackeen et al. . |
| 4,959,048 | 9/1990 | Seder et al. . |
| 5,049,142 | 9/1991 | Herrick et al. . |
| 5,131,906 | 7/1992 | Chen . |
| 5,163,959 | 11/1992 | Herrick . |
| 5,171,270 | 12/1992 | Herrick . |

OTHER PUBLICATIONS

Brochure of Lacrimedics, Inc., Rialto, California, "Patient-Proven Herrick Lacrimal Plugs," Dated 1992.
Brochure of Eagle Vision, Inc., Memphis, Tennessee, "Punctum Plugs," Dated 1990.

*Primary Examiner*—Gary Jackson
*Attorney, Agent, or Firm*—Poms, Smith, Lande & Rose

[57] ABSTRACT

A punctum plug used to temporarily close the punctal openings of the eye. The plug has a cap, a shaft, and a hollow bulb portion. The cap and shaft have an internal bore therein. A tool may be inserted into the bore so that the bulb portion is elongated and stretched, allowing the plug to be inserted into a punctal opening and into its lacrimal duct. The tool is then withdrawn from the plug, allowing the bulb portion to return to its original configuration, which effectively anchors the plug in the duct. An elongated shaft is used for another embodiment of the plug, which allows the plug to be inserted deeper into a duct. In yet another embodiment, a coiled body portion is used in place of the bulb portion. The insertion tool is used to stretch or uncoil the coiled body portion so that the plug may be inserted into a lacrimal duct. Withdrawal of the insertion tool allows the body portion to return to its original coiled configuration, anchoring the plug in the duct.

19 Claims, 3 Drawing Sheets

PUNCTUM PLUG

BACKGROUND OF THE INVENTION

The present invention relates generally to plugs used for treatment of the human eye, and more particularly to removable plugs used to temporarily close the punctal openings of the eye for treatment of the symptoms of dry eyes, and other symptoms related to tear drainage into the nasal lacrimal duct.

In the past, various different plugs, implants or other devices have been used to treat keratoconjunctivitis sicca, or dry eyes, and to decrease or stop tear drainage into the nasal lacrimal duct, which may cause such diverse symptoms as post nasal drip, sinusitis, allergies, headaches, snoring, etc. For example, U.S. Pat. Nos. 5,171,270, issued to Herrick on Dec. 15, 1992, and No. 5,163,959, issued to Herrick on Nov. 17, 1992, disclose an implant adopted to be inserted into the lacrimal duct of an eye. The implant has an elongated member having a medial tapered end and a collapsible flared flange attached to the opposite lateral end of the elongated member. The tapered end facilitates inserting the implant into the duct. The implant is placed into the lacrimal duct by inserting a tool into the collapsible flared flange and forcing the implant into the duct. As the implant is inserted, the collapsible flared flange collapses, and the flange engages the interior walls of the canaliculus.

Another implant is disclosed in U.S. Pat. Nos. 5,049,142, issued to Herrick et al. on Sep. 17, 1991, and No. 4,660,546, issued to Herrick et al. on Apr. 28, 1987. These patents describe a piece of catgut which may be inserted into the canaliculus. The catgut will swell in the canaliculus, and remain in place before it dissolves. A cylindrical implant may be used, which has a conically-shaped front portion to facilitate insertion into the canaliculus. The implant may have passageways therein to permit varying amounts of tears to pass through it. The implant may also be made from nonabsorbable materials, such as rubber or plastic.

U.S. Pat. No. 4,959,048, issued to Seder et al. on Sep. 25, 1990, discloses a lacrimal duct occluder having a shaft, a rounded cap attached to one end of the shaft, one or more conical segments attached to the other end of the shaft, and a rounded tip. The occluder is formed from a flexible, inert, non-toxic, medical grade silicone elastomer, and may be bent to conform to the shape of the lacrimal duct.

A punctum plug for controlling flow of lacrimal fluid through the tear ducts of an eye is described in U.S. Pat. No. 4,915,684 issued to MacKeen et al. on Apr. 10, 1990. The plug has a generally cylindrical body portion, a rounded head portion at one end thereof, and one or two peripheral members at the other end. The peripheral members are frustrum-shaped to facilitate inserting the plug into a duct, and retaining the plug in the duct.

Another punctum plug is disclosed in U.S. Pat. No. 3,949,750, issued to Freeman on Apr. 13, 1976. The punctum plug has a projecting tip or barb portion which dilates and blockingly protrudes into the canaliculus, a middle body or waist portion of smaller diameter around which the punctal sphincter ring tightens, and a larger smooth head portion. The plug is inserted by first dilating the punctal opening and canaliculus using a dilator tool, and then inserting the plug using a forceps or inserter tool.

A replacement tube for the lacrimal ducts is disclosed in U.S. Pat. No. 3,726,284, issued to Parker on Apr. 10, 1973. The tube is fabricated from glass or stiff plastic. It has elongated end portions and an expanded portion near the middle of the tube, which joins the elongated portions. The elongated portions and expanded portion have drain passages passing therethrough. A combined punctum plug dilator and insertion tool is shown in U.S. Pat. No. Des. 295,445, issued to Freeman on Apr. 26, 1988.

Other plugs or devices used for purposes other than treatment of the human eye are disclosed in U.S. Pat. Nos. 5,131,906, issued to Chen on July 21, 1992 (incontinence device); 4,281,658, issued to Child on Aug. 4, 1981 (dilator for teat of mammal); No. 3,858,571, issued to Rudolph on Jan. 7, 1975 (cornual plug used to obstruct entry to Fallopian tubes); No. 3,721,229, issued to Panzer on Mar. 20, 1973 (obturator device for injection of radiopaque substances into body cavity); No. 3,703,898, issued to Zackheim on Nov. 28, 1972 (teat dilator); and No. 3,463,141, issued to Mozolf on Aug. 26, 1969 (male contraceptive device).

SUMMARY OF THE INVENTION

It is an object of this invention to provide a punctum plug, which may be used to temporarily close the punctal openings of an eye to conserve human tears in order to treat dry eyes, and relieve other symptoms related to tear drainage into the nasal lacrimal duct.

It is another object of this invention to provide a punctum plug, which may be easily inserted into and securely anchored in the lacrimal ducts of a human eye.

It is still another object of this invention to provide a punctum plug, which may be easily removed from the lacrimal ducts of a human eye.

It is still another object of this invention to provide a punctum plug, which is economical to manufacture.

These and other objects and advantages are attained by a punctum plug having a cap, a shaft, and a hollow bulb portion. The cap and shaft have an internal bore therein. A tool may be inserted into the bore so that the bulb portion is elongated and stretched, allowing the plug to be inserted into a punctal opening and into its lacrimal duct. The tool is then withdrawn from the plug, allowing the bulb portion to return to its original configuration, which effectively anchors the plug in the duct. An elongated shaft is used for another embodiment of the plug, which allows the plug to be inserted deeper into a duct. In yet another embodiment, a coiled body portion is used in place of the bulb portion. The insertion tool is used to stretch or uncoil the coiled body portion so that the plug may be inserted into a lacrimal duct. Withdrawal of the insertion tool allows the body portion to return to its original coiled configuration, anchoring the plug in the duct.

The various features of the present invention will be best understood together with further objects and advantages by reference to the following description of the preferred embodiments when taken in conjunction with the accompanying drawings.

DESCRIPTION OF THE PREFERRED EMBODIMENT

The following specification taken in conjunction with the drawings sets forth the preferred embodiments of the present invention in such a manner that any person skilled in the art can make and use the invention. The embodiments of the invention disclosed herein are the best modes contemplated by the inventors for carrying out their invention in a commercial environment, although it should be understood that various modifications can be accomplished within the parameters of the present invention.

Figure 1:
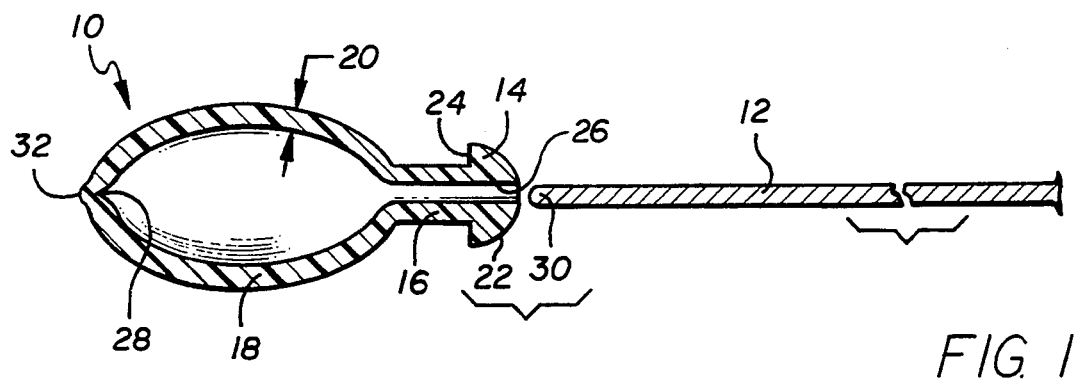
FIG. 1 is a longitudinal cross-sectional view of a punctum plug and insertion tool of the present invention.

FIG. 1 shows a punctum plug 10 and insertion tool 12 of the present invention. The punctum plug 10 has a cap 14 attached to a shaft 16, which, in turn, is attached to a hollow bulb portion 18 of wall thickness 20. The cap 14 preferably has a smooth convex surface 22, and a flat surface 24 as shown in FIG. 1. A bore 26 passes longitudinally through the cap 14 and shaft 16. A tapered tip or end 32 is used at the end of portion 18.

Figure 2:
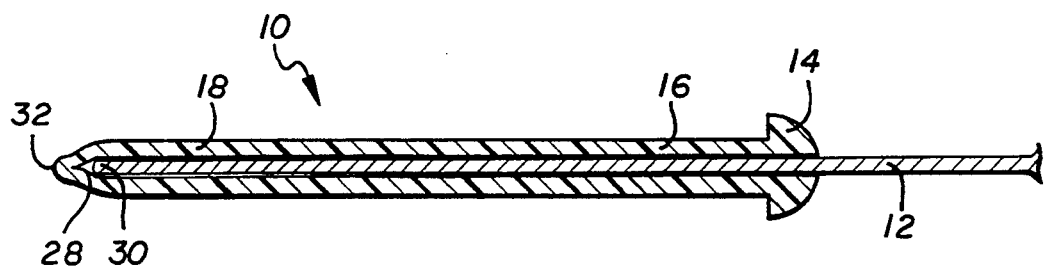
FIG. 2 is a view taken like FIG. 1, showing how the insertion tool may be inserted into the punctum plug of FIG. 2 for the purpose of stretching and elongating the plug for insertion into a lacrimal duct of a human eye.

The punctum plug 10 is preferably made out of silicone rubber. However, any other suitable elastic, resilient, nonallergenic, biocompatible or biologically inert material may be used, which may be inserted into a lacrimal duct of a human eye. The cap 14 is preferably about 3 mm in diameter. Bore 26 is about 0.1 mm in diameter. Any suitable thickness 20 may be used that will allow the bulb portion 18 to be stretched as shown in FIG. 2.

Alternatively, instead of a hollow bulb, portion 18 may be formed by two generally arcuate-shaped members (not shown) joined at first ends to the shaft 16, and together at the other ends thereof, forming a tapered end at 32. Such generally arcuate-shaped members may have the general cross-sectional shape shown in FIG. 1 or any suitable shape. The arcuate-shaped members would be about 0.4 mm thick or wide, or may have a diameter of about 0.4 mm. Any desirable longitudinal length may be used for the arcuate-shaped members. For each alternative embodiment, end 32 would be tapered to facilitate insertion of the plug 10 into a punctal opening of an eye.

Figure 3:
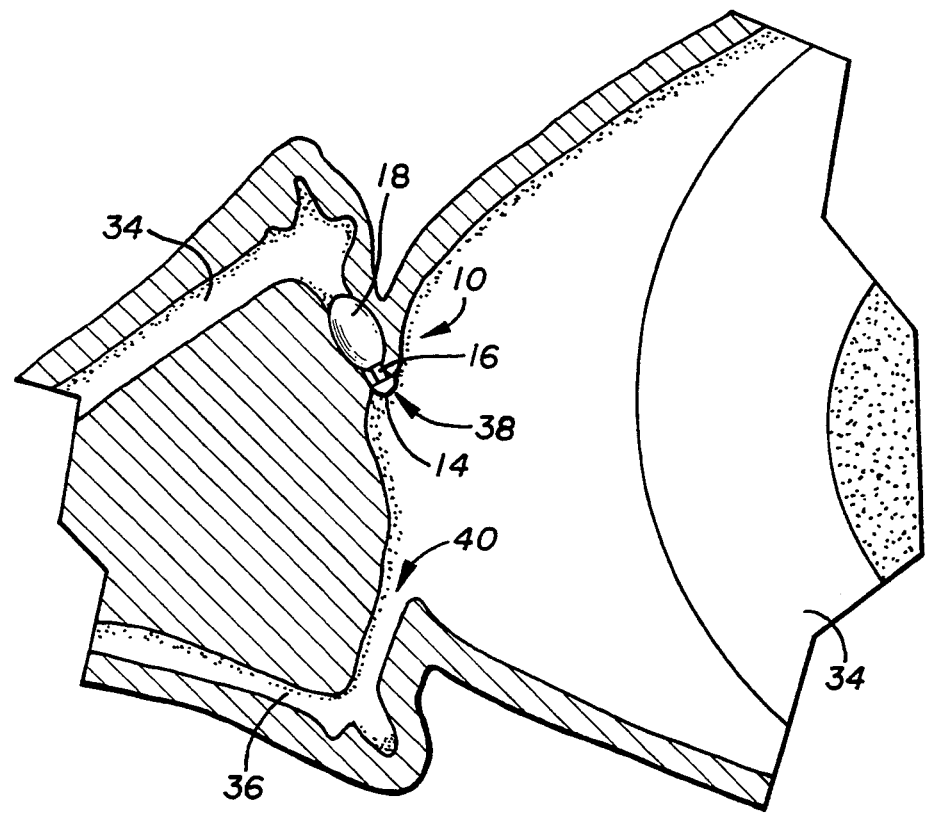
FIG. 3 is a partial cross-sectional view, showing the lacrimal system of a human eye and the punctum plug of FIG. 1 after insertion into a lacrimal duct for the purpose of closing a punctal opening of the duct.

Referring now to FIG. 3, the lacrimal system for a human eye 34 is shown, having upper and lower lacrimal ducts 34 and 36, respectively. The lacrimal ducts 34 and 36 drain tears or lacrimal fluid to the nasal duct or lacrimal sack (not shown). The upper and lower ducts 34 and 36 have punctal openings 38 and 40, respectively, through which tears enter and drain down the ducts toward the lacrimal sack.

The punctum plug 10 is used to close the punctal openings 38 and 40. This is accomplished by inserting tool 12 into bore 26 and into bulb portion 18 until end 30 of the tool 12 comes into contact with the inside of portion 18 at 28. The tool 12 is then used to push the plug 10 into one of the openings 38 and 40 and into one of the ducts 34 and 36, until surface 24 of the cap 14 comes into contact with tissue surrounding the punctal opening. As such, the cap 14 prevents the plug 10 from being pushed too far into the duct. As the plug 10 is pushed into one of the ducts 38 and 40, the bulb portion 18 stretches and elongates as illustrated in FIG. 2, which facilitates pushing the plug into the duct. Tapered end 32 also facilitates pushing the plug 10 into the duct.

After the plug 10 is pushed into one of the ducts 38 and 40, the insertion tool 12 is then withdrawn from the plug, and the bulb portion 18 returns to its original shape or configuration as shown in FIG. 3. As bulb portion 18 returns to its original shape, portion 18 contacts the inner walls or surfaces of the duct, effectively anchoring the plug 10 in place in the duct.

The elastic, resilient material used for the punctum plug 10 allows the plug to return to its original configuration after tool 12 is removed. The plug 10 may be easily removed from the duct by using forceps, tweezers, or some other tool to grasp the cap 14 and pull the plug out of the duct.

The diameter of the insertion tool 12 is preferably slightly smaller than 0.1 mm.

Figure 4:
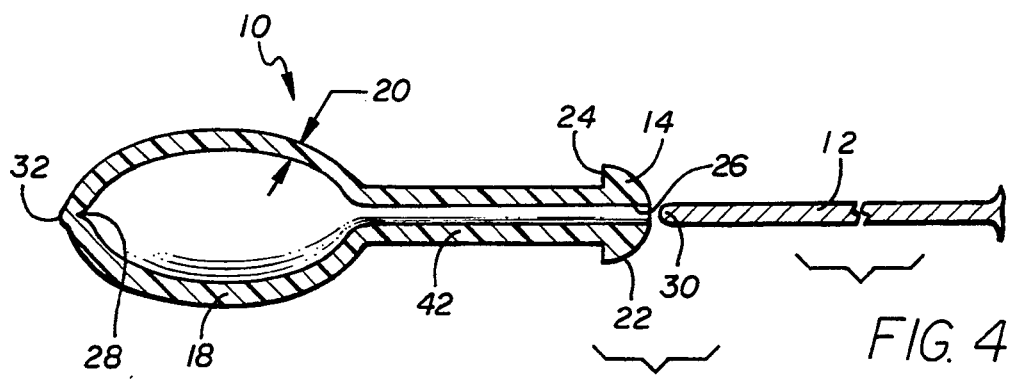
FIG. 4 is a longitudinal cross-sectional view of another embodiment of a punctum plug, having an elongated shaft, and of an insertion tool of the present invention.
Figure 5:
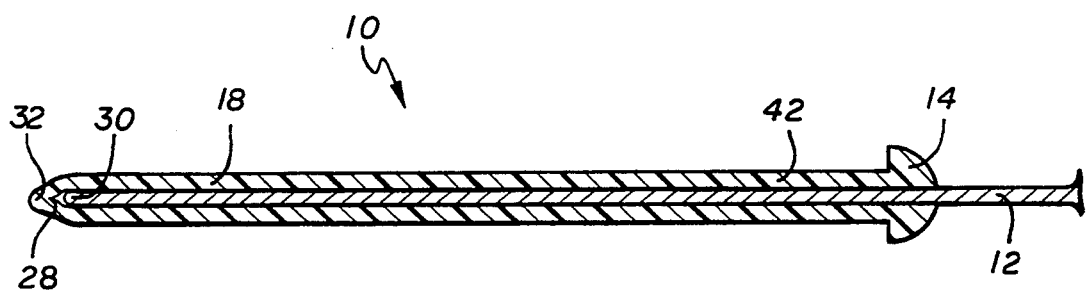
FIG. 5 is a view taken like FIG. 4, showing how the insertion tool may be inserted into the punctum plug of FIG. 4 for the purpose of stretching and elongating the plug for insertion into a lacrimal duct of a human eye.
Figure 6:
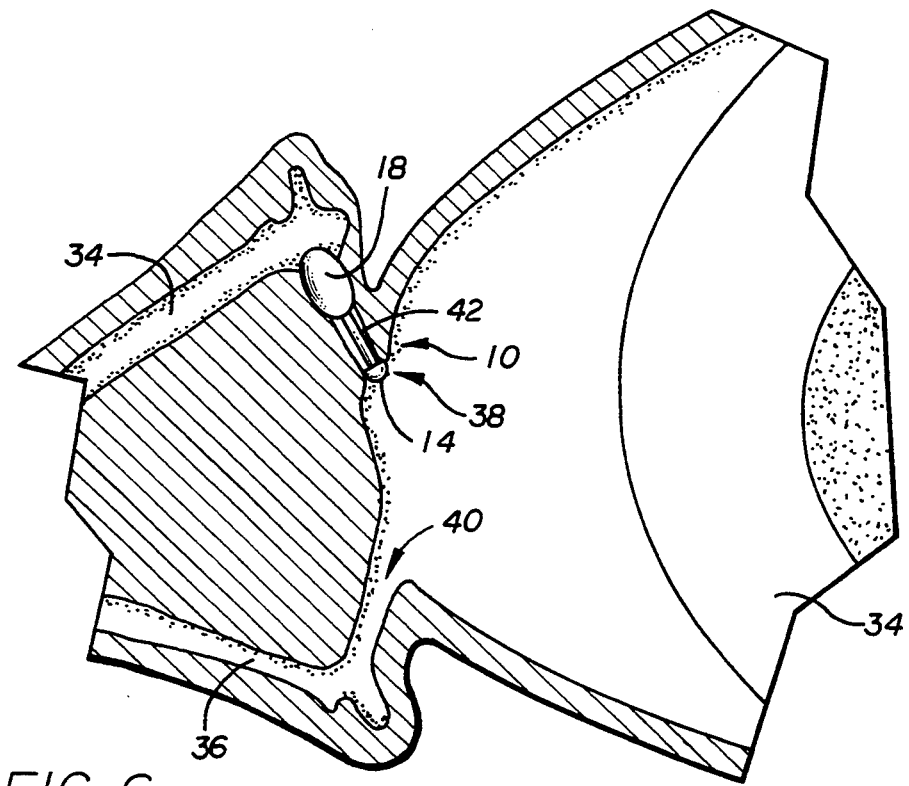
FIG. 6 is a view taken like FIG. 3, showing the punctum plug of FIG. 4 after insertion into a lacrimal duct for the purpose of closing a punctal opening of the duct.

FIG. 4 shows another embodiment of the punctum plug 10 having an elongated shaft 42. Except for the shaft 42, the plug 10 of FIG. 4 is like the plug 10 of FIG. 1. The elongated shaft 42 allows the plug 10 to be inserted deeper or farther into one of the lacrimal ducts 34 and 36 as shown in FIG. 6. Tool 12 is used to insert the plug 10 of FIG. 4 into the duct as explained above.

Figure 7:
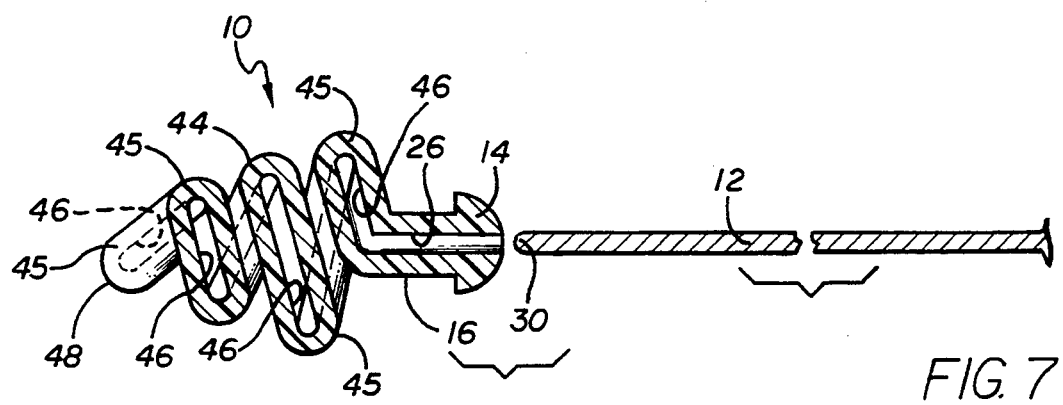
FIG. 7 is a longitudinal cross-sectional view of another embodiment of a punctum plug, having a coiled body portion, and of an insertion tool of the present invention.

Another embodiment of the punctum plug 10 is shown in FIG. 7. This embodiment has a coiled body portion 44 having any desirable number of coiled sections 45. Each coiled section 45 has an internal bore or aperture 46, which is in communication with the aperture 46 of its adjacent section. The plug 10 also has a shaft 16 and cap 14 like the shaft 16 and cap 14 used for the embodiments of FIGS. 1 and 4. Also, bore 26 passing through the cap 14 and shaft 16 is preferably the same size as aperture 46, and is in communication with aperture 46 of coiled section 45 attached to shaft 16. End 48 of the coiled body portion 44 may be rounded as shown, or may be tapered to facilitate inserting the plug into one of the lacrimal ducts 34 and 36.

Figure 8:
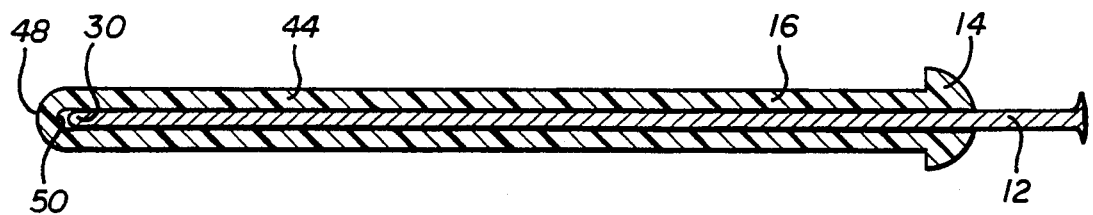
FIG. 8 is a view taken like FIG. 7, showing how the insertion tool may be inserted into the punctum plug of FIG. 7 for the purpose of stretching and elongating the plug for insertion into a lacrimal duct of a human eye.

The insertion tool 12 is used to insert the punctum plug 10 of FIG. 7 into one of the ducts 34 and 36 by inserting the tool 12 into bore 26 and aperture 46 so that end 30 of the tool 12 comes into contact with the coiled body portion 44 at 50, and the coiled body portion 44 uncoils or straightens as shown in FIG. 8. The tool 12 may then be used to insert the stretched and straightened punctum plug 10 into one of the punctal openings 38 and 40 and its corresponding duct 34 and 36.

Figure 9:
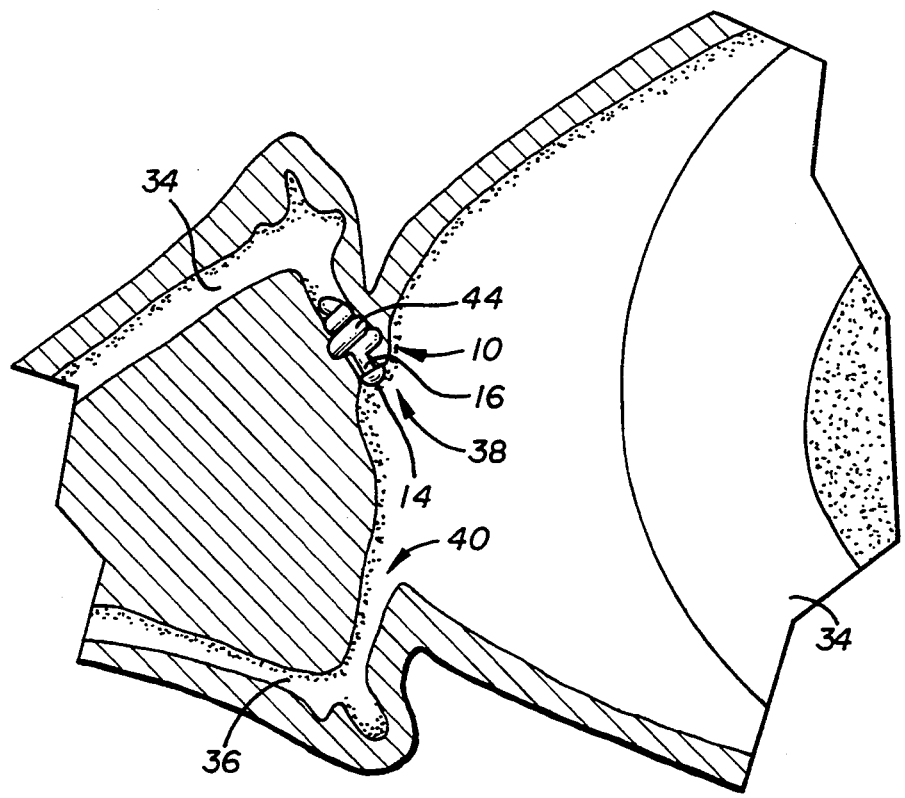
FIG. 9 is a view taken like FIG. 3, showing the punctum plug of FIG. 7 after insertion into a lacrimal duct for the purpose of closing a punctal opening of the duct.

After the punctum plug 10 is inserted into one of the ducts 34 and 36, the insertion tool 12 may then be withdrawn from the plug 10. The coiled body portion 44 will then return to its original coiled configuration as shown in FIG. 7. As portion 44 returns to its original shape, the coiled sections 45 contact the inner walls or surfaces of the duct, anchoring the plug 10 in place in the duct, as shown in FIG. 9. The resilient material used for the punctum plug 10 allows the coiled body portion 44 to return to its original coiled shape.

Preferably, the diameter of coiled body portion 44 is about 2 mm, and the coiled body portion 44, when straightened or stretched as shown in FIG. 8, has a length of about 6 mm. However, any suitable dimensions may be used for the embodiments of the punctum plug 10 shown in FIGS. 1, 4 and 7.

The above description discloses the preferred embodiments of the present invention. However, persons of ordinary skill in the art are capable of numerous modifications once taught these principles. Accordingly, it will be understood by those skilled in the art that changes in form and details may be made to the above-described embodiments without departing from the spirit and scope of the invention.

We claim:

1. A punctum plug for closing a punctal opening of a lacrimal duct of the human eye, comprising:
   a cap;
   a shaft attached to said cap, said cap and shaft having an aperture passing therethrough; and
   a resilient body portion attached to said shaft, said body portion adapted to be stretched and elongated from an original configuration by a tool engaging said aperture for insertion into said duct and closing of said punctal opening, and adapted to return to said original configuration after removal of said tool in order to anchor said plug in said duct;
   wherein said resilient body portion is a coiled body portion.

2. The punctum plug of claim 1 wherein said cap has a rounded surface.

3. The punctum plug of claim 1 wherein said coiled body portion has coiled sections with apertures therein.

4. A punctum plug for closing a punctal opening of a lacrimal duct of the human eye, comprising:
   a cap;
   a shaft attached to said cap and said shaft having an aperture passing therethrough;
   a resilient coiled body portion attached to said shaft, said body portion adapted to be stretched and elongated from an original coiled configuration by a tool engaging said aperture for insertion into said duct and closing of said punctal opening, and adapted to return to said original coiled configuration after removal of said tool in order to anchor said plug in said duct.

5. The punctum plug of claim 4 wherein said shaft is an elongated shaft.

6. The punctum plug of claim 4 wherein said cap has a rounded surface.

7. The punctum plug of claim 4 wherein said resilient coiled body portion has a tapered end.

8. The punctum plug of claim 4 wherein said resilient coiled body portion has coiled sections with apertures therein.

9. A puncture plug for closing a punoral opening of a lacrimal duct of a human eye, comprising:
   an enlarged cap having a cap through-opening;
   a tube having a tube through-passage;
   wherein said cap is permanently affixed to said tube such that said through-opening and said through-passage are aligned;
   wherein said cap has a rounded rearward surface anti a generally fiat forward surface;
   a resilient body portion secured to said tube and having a hollow interior and an opening communicating with said tube through-passage;
   wherein said body portion has a normal rounded bulbous configuration;
   an elongate tool;
   wherein said body portion is stretchable to an elongate configuration by insertion of said elongate tool in through said through-opening and application of pressure against a forward surface of said hollow interior;
   wherein said body portion when in the elongate configuration is insertable into a lacrimal duct of a human eye and thereby into an inserted position;
   wherein said body portion when in the inserted position resiliently returns to the bulbous configuration upon removal of said tool therefrom to anchor said body portion in the duct; and
   wherein said fiat forward surface of said cap contacts tissue surrounding the punctal opening with said body portion in the inserted position.

10. The punctum plug of claim 9 wherein said body portion has a forward tapered end.

11. A punctum plug system for closing a punctal opening of a lacrimal duct of a human eye, comprising:
    an enlarged cap;
    an elongate shaft attached to said cap, said cap and said shaft having an aperture passing therethrough;
    a resilient hollow body portion attached to said shaft and stretchable, when a stretching force is exerted thereon, from a natural bulbous configuration to an elongate stretched configuration and back to the bulbous configuration upon release of the stretching force;
    wherein said cap, said shaft and said body portion together form a puncture plug; and
    elongate tool means for insertion into and through said aperture and into said body portion to thereby exert the stretching force on said body portion for inserting said body portion into a lacrimal duct of a human eye and closing the punctal opening of the eye and for subsequent removal from said body portion and said aperture such that said body portion returns to the bulbous configuration to thereby anchor said body portion in the duct, wherein said punctum plug is in an inserted position.

12. The punctum plug system of claim 11 wherein said body portion has a tapered end opposite to said shaft.

13. The punctum plug system of claim 11 wherein said cap has a rounded rearward surface.

14. The punctum plug system of claim 13 wherein said cap has a generally fiat rearward surface which contacts tissue surrounding the punctal opening with said punctum plug in the inserted position.

15. A method for closing a punctal opening of a lacrimal duct of a human eye, comprising the steps of:

providing a puncture plug having a cap, an elongate shaft attached to the cap and a resilient hollow body portion attached to the shaft at an opposite end thereof, wherein an aperture passes through the cap and the shaft and into the body portion;

inserting an elongate tool into the aperture and thereby stretching the body portion from a normal bulbous configuration to an elongate configuration;

with the tool in the aperture and the body portion in the elongate configuration, inserting the body portion into a punctal opening and a distance into the lacrimal duct of a human eye and thereby into an inserted position; and with the body portion in the inserted position, removing the tool from the punctum plug and thereby allowing the body portion to resiliently return to the bulbous configuration engaging the duct walls and anchoring the plug in place in the duct.

16. The method of claim 15 wherein said inserting step includes manipulating the tool.

17. The method of claim 16 wherein said inserting step includes contacting a forward surface of the cap against tissue surrounding the punctal opening.

18. The method of claim 15 further comprising after said tool removing step, withdrawing the body portion from the duct.

19. The method of claim 18 wherein said withdrawing step includes grasping the cap with a tool and pulling the plug out of the duct.

* * * * *